US009149535B2

(12) United States Patent
Xu et al.

(10) Patent No.: US 9,149,535 B2
(45) Date of Patent: Oct. 6, 2015

(54) POLYMERS AND THE PREPARATION OF NANOGEL DRUG COCKTAILS

(71) Applicants: Peisheng Xu, Chapin, SC (US); Remant Bahadur K.C., Columbia, SC (US)

(72) Inventors: Peisheng Xu, Chapin, SC (US); Remant Bahadur K.C., Columbia, SC (US)

(73) Assignee: University of South Carolina, Columbia, SC (US)

( * ) Notice: Subject to any disclaimer, the term of this patent is extended or adjusted under 35 U.S.C. 154(b) by 326 days.

(21) Appl. No.: 13/929,981

(22) Filed: Jun. 28, 2013

(65) Prior Publication Data
US 2014/0011760 A1   Jan. 9, 2014

Related U.S. Application Data

(60) Provisional application No. 61/655,594, filed on Jun. 28, 2012.

(51) Int. Cl.
| | | |
|---|---|---|
| A61K 47/42 | (2006.01) | |
| A61K 47/32 | (2006.01) | |
| C08F 216/04 | (2006.01) | |
| C08F 8/34 | (2006.01) | |
| C08F 226/06 | (2006.01) | |
| A61K 9/51 | (2006.01) | |
| A61K 47/48 | (2006.01) | |
| C08F 8/04 | (2006.01) | |

(52) U.S. Cl.
CPC ............... *A61K 47/42* (2013.01); *A61K 9/5138* (2013.01); *A61K 47/32* (2013.01); *A61K 47/48238* (2013.01); *A61K 47/48784* (2013.01); *C08F 8/34* (2013.01); *C08F 216/04* (2013.01); *C08F 226/06* (2013.01); *C08F 8/04* (2013.01); *C08F 2810/20* (2013.01)

(58) Field of Classification Search
CPC ............................ C08F 216/04; C08F 226/06
See application file for complete search history.

(56) References Cited

PUBLICATIONS

Liu, J. et al. "Direct Synthesis of Pyridyl Disulfide-Terminated Polymers by RAFT Polymerization", Macromolecular Rapid Communications 2007, 28(3), 305-314.*

Butters, D. J.; Ghersi, D.; Wilcken, N.; Kirk, S. J.; Mallon, P. T., Addition of drug/s to a chemotherapy regimen for metastatic breast cancer. *Cochrane Database Syst Rev* 2010, 11, CD003368.

Lehar, J.; Krueger, A. S.; Avery, W.; Heilbut, A. M.; Johansen, L. M.; Price, E. R.; Rickles, R. J.; Short Iii, G. F.; Staunton, J. E.; Jin, X.; Lee, M. S.; Zimmermann, G. R.; Borisy, A. A., Synergistic drug combinations tend to improve therapeutically relevant selectivity. *Nat Biotech* 2009, 27 (7), 659-666.

Maeda, H.; Wu, J.; Sawa, T.; Matsumura, Y.; Hori, K., Tumor vascular permeability and the EPR effect in macromolecular therapeutics: a review. *J Control Release* 2000, 65 (1-2), 271-84.

(Continued)

*Primary Examiner* — Richard A Huhn
(74) *Attorney, Agent, or Firm* — Dority & Manning, P.A.

(57) ABSTRACT

Methods for forming, modifying, and drug loading of a copolymer are provided, along with the resulting products. The method can include polymerizing 2-(pyridin-2-yldisulfanyl)ethyl acrylate with poly(ethylene glycol)methacrylate via free radical polymerization to form the copolymer. The molar ratio of 2-(pyridin-2-yldisulfanyl)ethyl acrylate to poly(ethylene glycol)methacrylate is about 100:1 to about 1:100. After polymerizing, the copolymer can be reacted with a thiol monomer that contains a carbon-bonded sulfhydryl to modify end groups on a first portion of the 2-(pyridin-2-yldisulfanyl) ethyl acrylate repeating units. Thereafter, the copolymer can be crosslinked, and a drug can then be loaded into the crosslinked copolymer.

20 Claims, 14 Drawing Sheets

(56) References Cited

PUBLICATIONS

Iyer, A. K.; Khaled, G.; Fang, J.; Maeda, H., Exploiting the enhanced permeability and retention effect for tumor targeting. *Drug Discovery Today* 2006, 11 (17-18), 812-818.

Fang, J.; Nakamura, H.; Maeda, H., The EPR effect: Unique features of tumor blood vessels for drug delivery, factors involved, and limitations and augmentation of the effect. *Adv Drug Deliv Rev* 2010.

Maeda, H., Tumor-selective delivery of macromolecular drugs via the EPR effect: background and future prospects. *Bioconjug Chem* 2010, 21 (5), 797-802.

Fang, J.; Sawa, T.; Maeda, H., Factors and mechanism of "EPR" effect and the enhanced antitumor effects of macromolecular drugs including SMANCS. *Adv Exp Med Biol* 2003, 519, 29-49.

Davis, M. E.; Chen, Z. G.; Shin, D. M., Nanoparticle therapeutics: an emerging treatment modality for cancer. *Nat Rev Drug Discov* 2008, 7 (9), 771-82.

Pridgen, E. M.; Langer, R.; Farokhzad, O. C., Biodegradable, polymeric nanoparticle delivery systems for cancer therapy. *Nanomedicine (Lond)* 2007, 2 (5), 669-80.

Nie, S.; Xing, Y.; Kim, G. J.; Simons, J. W., Nanotechnology applications in cancer. *Annu Rev Biomed Eng* 2007, 9, 257-88.

Everts, M., Thermal scalpel to target cancer. *Expert Rev Med Devices* 2007, 4 (2), 131-6.

Brannon-Peppas, L.; Blanchette, J. O., Nanoparticle and targeted systems for cancer therapy. *Adv Drug Deliv Rev* 2004, 56 (11), 1649-59.

Blanco, E.; Kessinger, C. W.; Sumer, B. D.; Gao, J., Multifunctional Micellar Nanomedicine for Cancer Therapy. *Exp. Biol. Med.* 2009, 234 (2), 123-131.

van Vlerken, L.; Duan, Z.; Little, S.; Seiden, M.; Amiji, M., Augmentation of Therapeutic Efficacy in Drug-Resistant Tumor Models Using Ceramide Coadministration in Temporal-Controlled Polymer-Blend Nanoparticle Delivery Systems. *The AAPS Journal* 2010, 12 (2), 171-180.

Xu, P.; Van Kirk, E. A.; Murdoch, W. J.; Zhan, Y.; Isaak, D. D.; Radosz, M.; Shen, Y., Anticancer efficacies of cisplatin-releasing pH-responsive nanoparticles. *Biomacromolecules* 2006, 7 (3), 829-35.

Ghosh, S.; Basu, S.; Thayumanavan, S., Simultaneous and Reversible Functionalization of Copolymers for Biological Applications†. *Macromolecules* 2006, 39 (17), 5595-5597.

Xu, P.; Gullotti, E.; Tong, L.; Highley, C. B.; Errabelii, D. R.; Hasan, T.; Cheng, J. X.; Kohane, D. S.; Yeo, Y., Intracellular drug delivery by poly(lactic-co-glycolic acid) nanoparticles, revisited. *Mol Pharm* 2009, 6 (1), 190-201.

Xu, P.; Van Kirk, E. A.; Zhan, Y.; Murdoch, W. J.; Radosz, M.; Shen, Y., Targeted charge-reversal nanoparticles for nuclear drug delivery. *Angew Chem Int Ed Engl* 2007, 46 (26), 4999-5002.

Panté, N.; Kann, M., Nuclear Pore Complex Is Able to Transport Macromolecules with Diameters of ~39 nm. *Molecular Biology of the Cell* 2002, 13 (2), 425-434.

Na, H. S.; Lim, Y. K.; Jeong, Y.-I.; Lee, H. S.; Lim, Y. J.; Kang, M. S.; Cho, C.-S.; Lee, H. C., Combination antitumor effects of micelle-loaded anticancer drugs in a CT-26 murine colorectal carcinoma model. *International Journal of Pharmaceutics* 2010, 383 (1-2), 192-200.

Chou, T.-C., Drug Combination Studies and Their Synergy Quantification Using the Chou-Talalay Method. *Cancer Research* 2010, 70 (2), 440-446.

\* cited by examiner

POLYMERS AND THE PREPARATION OF NANOGEL DRUG COCKTAILS

PRIORITY INFORMATION

The present application claims priority to U.S. Provisional Patent Application Ser. No. 61/665,594 titled "Preparation of Nanogel Cocktail and Its Application" of Xu, et al. filed on Jun. 28, 2012, the disclosure of which is incorporated by reference herein.

BACKGROUND

Anticancer drug combinations have attracted much attention and have been extensively explored in clinical studies for the treatment of various types of cancer. Due to the heterogeneity of a tumor, cancer cells exist at different cell cycles. Delivery of multiple therapeutic agents using a single carrier system can suppress the cancer growth, since the drugs can have specific activity based on the different growth cycle of a cancer cell. A drug cocktail, such as a combination of drugs with different anticancer mechanisms that act synergistically, should exhibit superior response and patient survival rate than any single agent. However, the translation of this theoretical advantage to benefit the patient is hindered by their associated side effects, which can include (i) the potent toxic drug combination can damage normal cells while it kills cancer cells, (ii) the potential drug-drug interaction can deteriorate patient health condition, and (iii) the consequence of side effect results in poor patient compliance.

In order to enhance the efficacy of anticancer drugs while attenuating their associated side effects, nanotechnology was introduced into the treatment of cancer. Nanoparticle related cancer targeting is mainly achieved by passive accumulation of drug-loaded nanoparticles through the leaky blood capillaries in the tumor tissue. It has been shown that those vasculature pore sizes could be as large as 400 nm, which allows the extravagation of nanoparticles to the cancer tissues. In addition, lymphatic deficiency develops during cancer's progression; as a consequence, the lymphatic drainage of the nanoparticles from the tumor tissue is inadequate. The synergic effect of the above mentioned characteristics of tumor tissue results in the passive accumulation of nano-sized particles. This phenomenon is referred to as enhanced permeability and retention effect (EPR) of cancer. It has been demonstrated that by taking advantage of the EPR effect, nanoparticles can preferentially deliver drugs to cancer tissues, and therefore significantly enhance the therapeutic efficacy while substantially reducing drug side effects. As such, a need exists for a nanocarrier that is stable in a physiological environment during circulation while intracellularly releasing its payload in a timely manner after entering the cancer cell.

SUMMARY

Objects and advantages of the invention will be set forth in part in the following description, or may be obvious from the description, or may be learned through practice of the invention.

Methods are generally provided for forming, modifying, and drug loading of a copolymer (e.g., a random copolymer, a block copolymer, etc.), along with the resulting products. In one embodiment, the method includes polymerizing 2-(pyridin-2-yldisulfanyl)ethyl acrylate with poly(ethylene glycol) methacrylate via free radical polymerization to form the copolymer. In this embodiment, the copolymer includes 2-(pyridin-2-yldisulfanyl)ethyl acrylate repeating units and poly(ethylene glycol)methacrylate repeating units. In one particular embodiment, the molar ratio of 2-(pyridin-2-yldisulfanyl)ethyl acrylate to poly(ethylene glycol)methacrylate is about 100:1 to about 1:100 (e.g., about 20:1 to about 1:20). The free radical polymerization can be initiated by 2,2-azobisisobutyronitrile or another suitable initiator.

After polymerizing, the method can, in certain embodiments, further include reacting the copolymer with a thiol monomer that contains a carbon-bonded sulfhydryl through a thiol-disulfide exchange reaction to modify end groups on a first portion of the 2-(pyridin-2-yldisulfanyl)ethyl acrylate repeating units. Thereafter, in particular embodiments, the method can further include crosslinking the copolymer via a thiol-disulfide exchange reaction to form a crosslinked copolymer. A drug (or a combination of drugs) can then be loaded into the crosslinked copolymer.

As stated, copolymers are also generally provided. In one embodiment, the copolymer comprises 2-(pyridin-2-yldisulfanyl)ethyl acrylate repeating units of Formula (III):

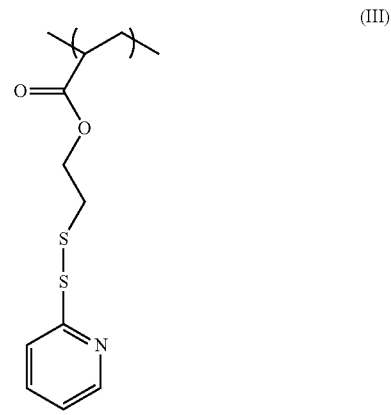

and poly(ethylene glycol)methacrylate repeating units of Formula (IV):

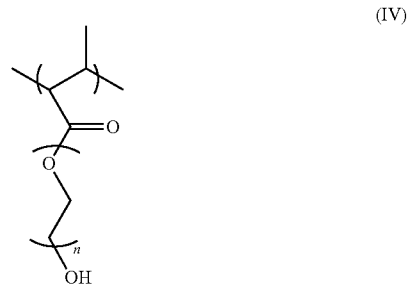

where n can be about 6 to about 3,000. The 2-(pyridin-2-yldisulfanyl)ethyl acrylate repeating units of Formula (III) and the poly(ethylene glycol)methacrylate repeating units of Formula (IV) can be present in the polymer in a molar ratio of about 100:1 to about 1:100 (e.g., about 20:1 to about 1:20). Such a copolymer can have a molecular weight of about 1,000 to about 100,000.

In one particular embodiment, the copolymer can further include modified disulfanyl repeating units of Formula (VI):

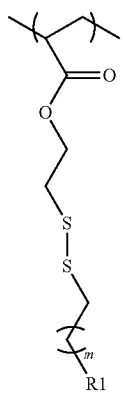

(VI)

where R1 is H, a hydroxyl group, a carboxyl group, an aldehyde group, an amine group, an amide group, an amino acid, a peptide chain of at least two amino acids, or another organic end group; and m is an integer of 1 to about 19. For example, the modified disulfanyl repeating units can be present in the copolymer in an amount that is about 1 molar % of the 2-(pyridin-2-yldisulfanyl)ethyl acrylate repeating units in the modified copolymer to about 50% of the 2-(pyridin-2-yldisulfanyl)ethyl acrylate repeating units in the modified copolymer.

The copolymer can, in certain embodiments, be crosslinked upon a portion of the 2-(pyridin-2-yldisulfanyl) ethyl acrylate repeating units. A nanogel is also generally provided that includes a drug loaded within such a crosslinked copolymer. The nanogel can be administered to a patient for targeted delivery of the drug to cancer cells.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 2B showing the size distribution of ND under the trigger of TCEP vs time acquired with Dynamic light scattering (the key is in order of the intensity peaks shifting from left to right); and FIG. 2C showing a TEM image of a ND nanoparticle after 5 hr treatment with 1 mM TCEP.

DEFINITIONS

Figure 1A:
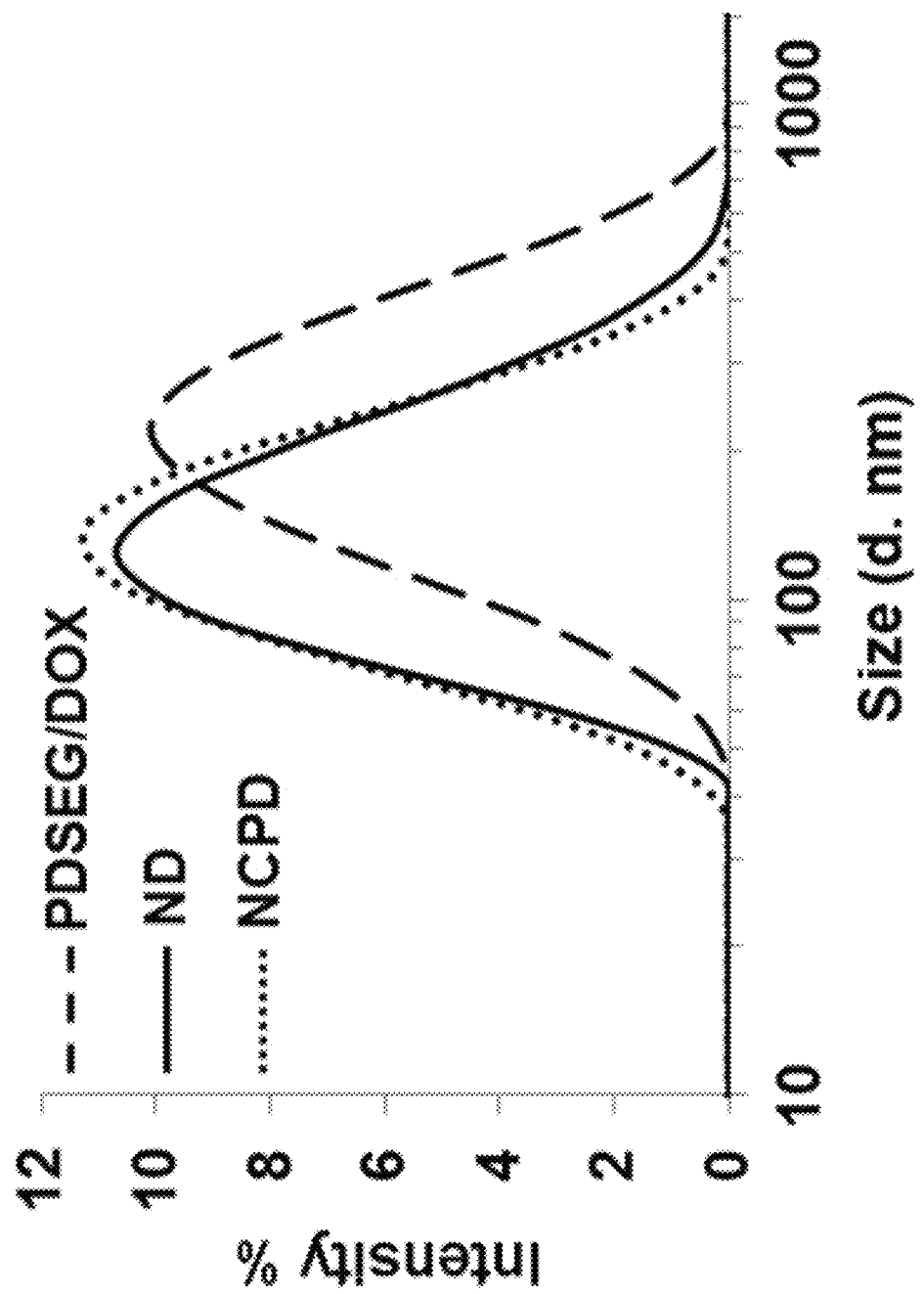
FIG. 1A shows size distribution curves of nanoparticles made from PDSEG polymer, doxorubicin loaded nanogel (ND,), and paclitaxel and doxorubicin loaded nano-cocktail (NCPD,) acquired by dynamic light scattering according to the Examples.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\sum_i N_i M_i}{\sum_i N_i}$$

where $N_i$ is the number of molecules of molecular weight $M_i$. The number average molecular weight of a polymer can be determined by gel permeation chromatography, viscometry (Mark-Houwink equation), and all colligative methods, like vapor pressure osmometry or end-group determination.

The "weight average molecular weight" ($M_w$) is readily calculated by one of ordinary skill in the art, and generally refers to:

$$\overline{M}_w = \frac{\sum_i N_i M_i^2}{\sum_i N_i M_i}$$

where $N_i$ is the number of molecules of molecular weight $M_i$. The weight average molecular weight can be determined by light scattering, small angle neutron scattering (SANS), X-ray scattering, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

An intracellular self-expanding drug delivery system, nano-cocktail (NC), is generally provided, along with methods of its formation and use. The drug delivery system is capable of delivering therapeutics specifically to tumor tissue while minimizing the drug release during circulation. In one particular embodiment, the drug delivery system is a NC nanogel that is responsive to both pH and redox potential such that the NC nanogel expands its size and releases the payload intracellularly. In vitro cytotoxicity experiments showed that NC nanogel exhibited a synergistic effect in killing cancer cells and exhibited higher anticancer efficiency than its free drug counterpart. Furthermore, the delivery system itself is non-toxic.

The NC system described herein is stable in the physiological environment while expanding its size and releasing its payload in intracellular. Through its self-expanding and dual responsive releasing properties, NC nanogel can minimize its side effects while enhancing its anticancer efficacy. In vitro MTT assay showed that NC nanogel exhibits much stronger synergistic effect in killing cancer cells than its free drug counterpart.

I. Synthesis of PDSEG

Figure 6A:
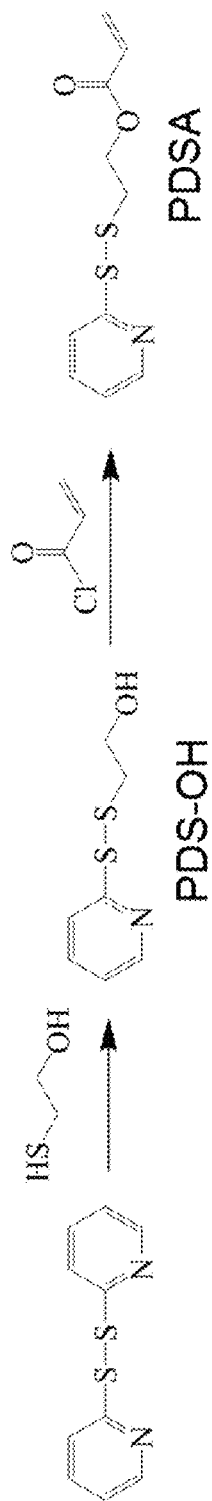
FIGS. 6A-6C are a schematic representation of the synthesis of RPDSEG polymer and fabrication of ND and NCPD nanoparticles.

As shown in FIG. 6A, a monomer of 2-(pyridin-2-yldisulfanyl)ethanol (PDS-OH) can be formed by reacting aldrithiol-2 and mercaptoethanol. Then, a monomer of 2-(pyridin-2-yldisulfanyl)ethyl acrylate (PDSA) can be prepared by coupling acryloyl chloride with PDS-OH. The resulting PDSA monomer has the general structure shown below:

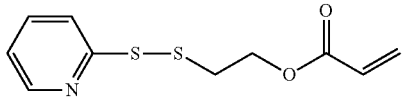

PDSA Monomer: Formula (I)

Poly[(2-(pyridin-2-yldisulfanyl)-co-[poly(ethylene glycol)]] (PDSEG) can then be formed generally from polymerization reaction between a plurality of PDSA monomers and a plurality of poly(ethylene glycol)methacrylate (PEGMA) monomers. In one embodiment, the poly(ethylene glycol) methacrylate monomer can have the structure:

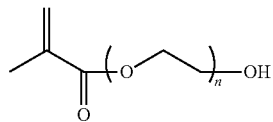

exemplary PEGMA monomer: Formula (II)

where n is about 6 to about 1,000, such as about 6 to about 100 (e.g., about 6 to about 20).

This reaction can be facilitated by any suitable catalyst. For example, the catalyst used in the reaction can be, in particular embodiments, azobisisobutyronitrile (AIBN), benzoyl peroxide, potassium persulfate, or combinations thereof. The polymerization can be free radical polymerization or living radical polymerization including stable free radical mediated polymerization (SFRP), atom transfer radical polymerization (ATRP), reversible addition-fragmentation chain transfer (RAFT) polymerization, and iodine-transfer polymerization.

As a result of such a polymerization, a PDSEG copolymer is formed having 2-(pyridin-2-yldisulfanyl)ethyl acrylate repeating unit according to Formula III and poly(ethylene glycol)methacrylate repeating units according to Formula IV:

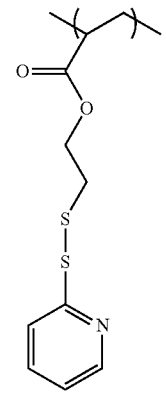

2-(pyridin-2-yldisulfanyl)ethyl acrylate repeating units: Formula (III)

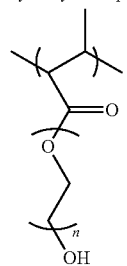

poly(ethylene glycol)methacrylate repeating units: Formula (IV)

where n is about 6 to about 3,000, such as about 6 to about 100 (e.g., about 6 to about 20).

In one embodiment, the molar ratio of the 2-(pyridin-2-yldisulfanyl)ethyl acrylate repeating units of Formula (III) to the poly(ethylene glycol)methacrylate repeating units of Formula (IV) is about 100:1 to about 1:100. In particular embodiments, the molar ratio of the 2-(pyridin-2-yldisulfanyl)acrylate repeating units of Formula (III) to poly(ethylene glycol)methacrylate repeating units of Formula (IV) is about 20:1 to about 1:20 (e.g., about 10:1 to about 1:10, such as about 1:1).

The PDSEG copolymer can generally have a weight average molecular weight that is about 1,000 to about 100,000 (e.g., about 5,000 to about 35,000) with a PDI of about 1.05 to about 2 (e.g., about 1.15 to about 1.30).

Figure 6B:
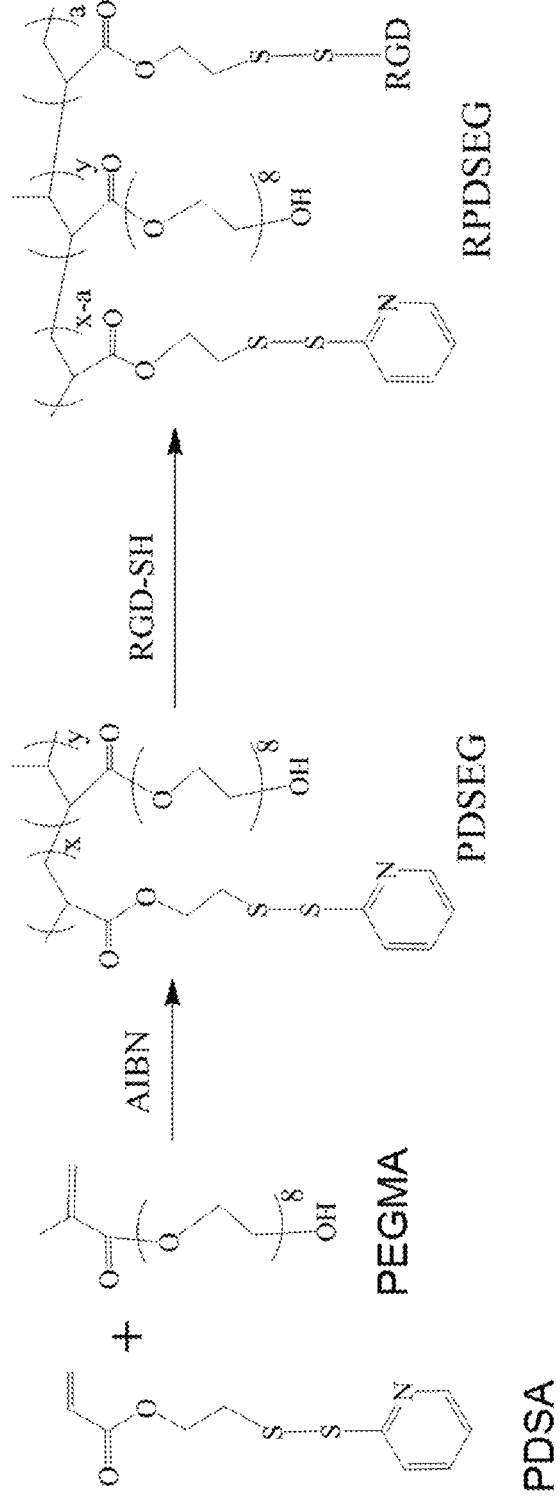

For example, in one particular embodiment, the PDSEG copolymer can be formed to have the formula shown in FIG. 6B (i.e., where n is 8). As discussed above, such a polymer can have a ratio of x to y that is about 100:1 to about 1:100 (i.e., the molar ratio of the PDSA monomer to the PEGMA monomer is about 100:1 to about 1:100). Although shown as a block copolymer in FIG. 6B, it is to be understood that this representation is simply shorthand for any type of copolymer (e.g., random, block, etc.) that includes repeating units of both the 2-(pyridin-2-yldisulfanyl)ethyl acrylate repeating units and the poly(ethylene glycol)methacrylate repeating units.

II. Synthesis of RPDSEG

The PDSEG polymer formed above can then be reacted with a thiol monomer that contains a carbon-bonded sulfhydryl (i.e., —C—SH or R—SH group where R represents an alkane, alkene, or other carbon-containing chain) through a thiol-disulfide exchange reaction to substitute a portion of the end groups of the PDSA monomer in the PDSEG copolymer. That is, a portion of the 2-(pyridin-2-yldisulfanyl)ethyl acrylate repeating units in the PDSEG copolymer are converted to be have a modified end group.

Any suitable thiol monomer can be utilized in the thiol-disulfide exchange reaction, including but not limited to, alkythiols having a carbon chain of about 2 to about 20 (e.g., ethanethiol, propanethiol, butanethiol, pentanethiol, etc.) with or without a functional end group opposite of the thiol group (e.g., a carboxylic group, a hydroxyl end group, an amine end group, etc.). In one embodiment, the thiol monomer can have the formula:

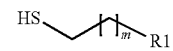

thiol monomer: Formula (V)

where m is 1 to 19 and R1 is H, a hydroxyl group (—OH), a carboxyl group (—COOH), an aldehyde group (—CHO), an amine group (—NH₂), an amide group (—CONH₂), an amino acid, a peptide chain of at least two amino acids (e.g., arginylglycylaspartic (RGD) acid), or another organic end group.

The reaction can take place by mixing PDSEG copolymer with thiol monomer in any suitable solvent for them such as water, methanol, ethanol, dimethyl sulfoxide, methylene chloride.

Through this reaction, about 1 molar % to about 50 molar % (e.g., about 5 molar % to about 25 molar %) of the 2-(pyridin-2-yldisulfanyl)ethyl acrylate repeating units of Formula (III) in the PDSEG copolymer can be converted with the thiol monomer that contains a carbon-bonded sulfhydryl through a thiol-disulfide exchange reaction to modify a portion of the end groups of the 2-(pyridin-2-yldisulfanyl)ethyl acrylate repeating units in the PDSEG copolymer. As such, the resulting modified PDSEG copolymer (RPDSEG) can include the modified disulfanyl repeating units in an amount that is about 1 molar % of the 2-(pyridin-2-yldisulfanyl)ethyl acrylate repeating units to about 50% of the 2-(pyridin-2-yldisulfanyl)ethyl acrylate repeating units in the modified copolymer.

Upon the exchange reaction, the resulting modified copolymer (RPDSEG) includes both the 2-(pyridin-2-yldisulfanyl)ethyl acrylate repeating units of Formula (III) to poly(ethylene glycol)methacrylate repeating units of Formula (IV), as well as modified disulfanyl repeating units of Formula (VI):

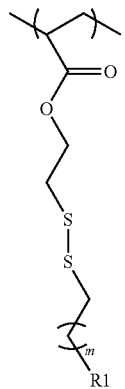

modified disulfanyl repeating units: Formula (VI)

where R1 is H, a hydroxyl group (—OH), a carboxyl group (—COOH), an aldehyde group (—CHO), an amine group (—NH₂), an amide group (—CONH₂), an amino acid, a peptide chain of at least two amino acids (e.g., arginylglycylaspartic (RGD) acid), or another organic end group as described above with respect to Formula (V); and m is an integer of 1 to about 19.

For example, in one particular embodiment, the RPDSEG polymer can be formed to have the formula shown in FIG. 6B (i.e., where n is 8, R1 is RGD, and m is 1). As discussed above, such a polymer can have a ratio of x to y that is about 100:1 to about 1:100 (i.e., the molar ratio of the PDSA monomer to the PEGMA monomer is about 100:1 to about 1:100) and a can be about 1% of x to about 50% of x (i.e., about 1 molar % to about 50 molar % (e.g., about 5 molar % to about 25 molar % of the PDSA monomer units). Although shown as a block copolymer in FIG. 6B, it is to be understood that this representation is simply short hand for any type of copolymer (e.g., random, block, etc.) that includes repeating units of the 2-(pyridin-2-yldisulfanyl)ethyl acrylate repeating units, the poly(ethylene glycol)methacrylate repeating units, and the modified disulfanyl repeating units.

III. Crosslinking of RPDSEG

The RPDSEG polymer can then be crosslinked via a second thiol-disulfide exchange reaction that bonds a portion of the remaining (i.e., unsubstituted) end groups of the PDSA monomer in the PDSEG polymer with each other. For example, the crosslinking reaction can occur via disulfide bonds cleavage followed by aerial oxidation.

In one embodiment, a crosslinking agent it utilized to facilitate the crosslinking within and between the RPDSEG polymers. Particularly suitable crosslinking agents include, but are not limited to, tris(2-carboxyethyl)phosphine (TCEP), dithiothreitol, glutathione, 1,2-ethanedithiol, 1,3-propanedithiol, 1,4-butanedithiol, 1,5-pentanedithiol, or a mixture thereof. The amount of crosslinking agent can be varied based on the type of crosslinking agent, the amount of crosslinking desired, etc.

Figure 6C:
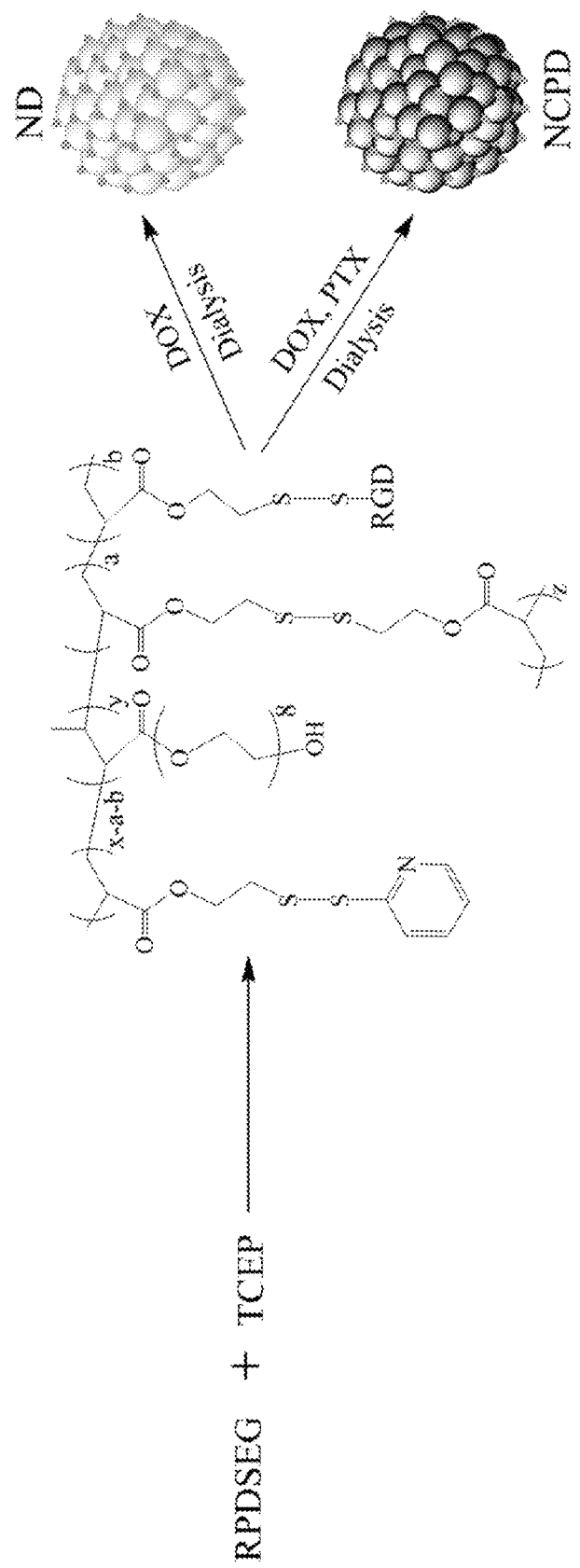

FIG. 6C shows an exemplary reaction scheme of such a crosslinking reaction.

Through this crosslinking reaction, a nanogel polymeric material is formed with intramolecular disulfide bonds resulting in the assembly of subcompartments while intermolecular disulfide bonds stabilize the multicompartment nanogel structure through disulfide bonds between subcompartments.

IV. Drug Loading of the Crosslinked RPDSEG

A drug (or a combination of drugs) can then be loaded into the crosslinked polymeric material via dialysis. For example, a drug or a combination of drugs can be dissolved in DMSO and mixed with PDSEG polymer DMSO solution. A predetermined amount of TCEP in DMSO can then be added to the above mixture and equilibrated for by stirring (e.g., for about 5 minutes to about 1 hour). Then, the mixture can be dropped into distilled water (and, in one particular embodiment, double distilled water) under stirring and kept stirring for aerial oxidation (e.g., for about 1 hour to about 10 hours). Unreacted TCEP, any reaction byproduct, and any remaining free drug can then be removed by repeated dialysis (e.g., using Spectra/Por® dialysis tube (MWCO, 1.0 KDa) against PBS (pH 8.0) for 4 hr and PBS (pH 7.4) for 4 hr at room temperature).

V. Delivery of the Drug(s)

The drug(s) loaded nanogels can be administered to a patient suffering from a cancerous tumor. For example, drug loaded nanogels can be suspended in saline and administered to a cancer patient through intravenous infusion or intravenous bolus injection.

EXAMPLES

A new type of polymer, poly[(2-(pyridin-2-yldisulfanyl)-co-[poly(ethylene glycol)]] (PDSEG), was developed that containing both ester and disulfide bonds, which are labile to acidic pH and redox potential, respectively. On this basis, a pH and redox dual responsive nanoparticle was fabricated and aimed to fully take advantage of its use in a drug cocktail while eliminating the toxic side effects associated with the drug combination.

In summary, a nano-cocktail delivery system, NCPD nanogel, was designed that is sensitive to both acidic pH and redox potential. NCPD has a multicompartment structure with a size around 134 nm and slightly negative surface charge. Drug loaded nanogels are stable in physiological environment while spontaneous swelling and fast releasing its payload after it entering cancer cells with the help of αVβ3 integrin mediated endocytosis. NCPD, due to its enhanced cellular uptake and dual responsive releasing property, displays much stronger synergism than its free drug counterpart. The above exciting findings indicate that NCPD could significantly attenuate the side effect of drug cocktail while achieving a boosted synergistic anticancer effect. Based on these promising in vitro results the further investigation will employ NCPD system for in vivo tumor growth inhibition experiment.

Methods

Synthesis of 2-(pyridin-2-yldisulfanyl)ethanol (PDS-OH)

The synthesis of 2-(pyridin-2-yldisulfanyl)ethanol (PDS-OH) was carried out using aldrithiol-2 and mercaptoethanol following the method designed by Ghosh et al. Briefly, 1.2 mL (0.02 mol) of mercaptoethanol was dissolved in 5 mL methanol and added drop wise to the solution of aldrithiol-2 (5.0 g, 0.02 mol) dissolved in methanol (25 mL) containing acetic acid (333 μL). The reaction mixture was degassed with argon for 20 min. and stirred at room temperature for 24 h. Then the solvent was evaporated under reduced pressure and the crude product (yellow oil) was purified by gravity column chromatography using silica gel (size 100 μm) as stationary phase and the mixture of ethyl acetate and hexane as mobile phase. The un-reacted aldrithiol-2 was eluted first with 15% ethyl acetate then the desired product was collected with 30% ethyl acetate. Finally, the eluent was evaporated under reduced pressure and the product was vacuum dried for 48 h. The structure of the PDS-OH was confirmed by $^1$H-NMR (Mercury Varian 400 NMR, Varian Inc., Palo Alto, Calif.) using $CDCl_3$ as solvent and TMS as internal standard. $^1$H-NMR spectra of PDS-OH showed methylene protons resonance peaks (—C$\underline{H}_2$—SH at δ~2.9 and —C$\underline{H}_2$—OH at 3.7 ppm) along with the aromatic protons at δ~7.12, 7.4, 7.56 and 8.5 ppm corresponding to pyridine rings.

Synthesis of 2-(pyridin-2-yldisulfanyl)ethyl acrylate (PDSA)

2-(pyridin-2-yldisulfanyl)ethyl acrylate (PDSA) was prepared by coupling acryloyl chloride with PDS-OH. Briefly, PDS-OH (1.0 g, 5.34 mmol) was dissolved in 100 mL anhydrous methylene chloride containing 5.7 mL triethylamine and the solution was cooled with ice-bath for 30 min. In the meantime, acryloyl chloride (725 mg, 8.01 mmol) was dissolved in 50 mL anhydrous methylene chloride and cooled with ice-bath for 30 min. After that, acryloyl chloride solution was added drop wise into PDS-OH solution under stirring under ice-bath and the reaction was kept at room temperature for 12 h. The TEA salt was removed by precipitating (3×) with ice cold ether and followed by acetate/hexane (30/70, v/v) as mobile phase. The structure of the monomer was confirmed by its appearance at δ~5.8, 6.0 and 6.4 ppm along with the characteristic resonances peaks of PDS-OH. The quantitative shifting of —C$\underline{H}_2$—OH resonance peaks (δ~3.7 ppm) to δ~4.4 ppm indicates the successful end capping of PDS-OH by generating ester groups. The integration ratio between pyridine ring proton (δ~7.12 ppm) and aryl proton (δ~5.8) was taken in account for the quantification of reaction efficiency.

Synthesis of Poly[(2-(pyridin-2-yldisulfanyl)-co-[poly(ethylene glycol)]](PDSEG)

Poly[(2-(pyridin-2-yldisulfanyl)-co-[poly(ethylene glycol)]] (PDSEG) copolymer was synthesized by free radical polymerization of 2(pyridin-2-yldisulfanyl)ethyl acrylate (PDSA) and poly(ethylene glycol)methacrylate (PEGMA). For PDSEG synthesis, PDSA (250 mg, 1.33 mmol) and PEGMA (478.8, 1.33 mmol) were dissolved in anisole (10 mL) and degassed with argon for 30 min. Then, 2,2-azobisisobutyronitrile (AIBN) (14.61 mg, 0.089 mmol dissolved in anisole) was added dropwise and the reaction mixture was stirred for 24 hr at 65° C. The final product was precipitated (3×) in ice cold ether and vacuum dried for 48 h. Structural composition of the polymer were analyzed by $^1$H-NMR, molecular weight (Mw) and polydispersity of PDSEG was evaluated by GPC (viscotek GPCmax VE 2001 GPC solvent/sample module, Viscotek VE 3580 RI detector and 270 Dual Detector) using THF as mobile phase. For the quantification of side chain functionality, PDSEG (1.0 mg/mL) was incubated with DTT (10 mM) for 1 h. at room temperature then the amount of 2-pyridinethione released was quantified through UV-Vis spectrophotometer (DU®650 Spectrophotometer, Beckman Coulter, USA) at λ=375 nm (ε, molar absorption coefficient=8080 $M^{-1}$ $cm^{-1}$). $^1$H-NMR spectroscopy of PDSEG polymer showed the characteristic proton resonance peaks corresponds to 2-pyridinethione (δ=7.0 to 8.5 ppm) and PEG (δ=3.6 ppm). The disappearance of the proton resonance peaks from δ=5.5 to 6.5 ppm clearly indicates the consumption of acryl bonds of monomers. Hydrophilic/hydrophobic ratio into the polymers was 1:1 (mol/mol) as quantified using the characteristic resonance peaks of pyridine proton (δ=8.5 ppm) and the PEG proton (δ=3.6 ppm). The molecular weight (Mw) of PDSEG was 26,431 Da with a PDI of 1.19 according to polystyrene standard.

Drug Encapsulation.

Disulfide bond cross-linked nanogels were fabricated from PDSEG polymer by disulfide bonds cleavage followed by aerial oxidation. Briefly, cRGD peptide (400 μg in 100 μL DMSO) was grafted onto PDSEG (4 mg, in 100 μL DMSO) polymer through thiol-disulfide exchange reaction. After 12 hr of reaction at room temperature, 250 μL of DOX (2 mg/mL, in DMSO containing 25 μL TEA) and 52 μL TCEP (2 mg/mL, in DMSO) were added to polymer solution and equilibrated for 15 min by stirring. Then the mixture was dropped into 4 mL ddH2O under stirring and kept stirring for aerial oxidation for 4 hr. Unconjugated cRGD, TCEP and free DOX were removed by repeated dialysis using Spectra/Por® dialysis tube (MWCO, 1.0 KDa) against PBS (pH 8.0) for 4 hr and PBS (pH 7.4) for 4 hr at room temperature. Finally drug loaded nanogel was filtered (0.45 μm syringe filter) and lyophilized using trehalose (5% w/v). To prepare the nano-cocktail, NCPD, DOX (500 μg) and PTX (500 μg) were mixed together with the polymer solution and the further process was done as above. For drug loading efficiency quantification, nanogels were dissolved in DMSO and UV absorbance was measured using UV-Vis spectroscopy (DU®650 Spectrophotometer, Beckman Coulter, USA) at λ=490 nm referencing to the DOX calibration curve in DMSO. The content of PTX in nanogel was quantified by HPLC Water 2695 attached with Water 2996 Photodiode Array Detector) using acetonitrile (60%) and ddH2O (40%) as mobile phase and Ascentis® C18 column (Dimension 25 cm×4.6 mm).

Nanogel Characterization.

The morphology, size distribution and the surface charge (ζ-potential), of the nanogel were determined by transmission electron microscopy (TEM) using Hitachi H-800 operated at 200 kV accelerating voltage and dynamic light scattering (DLS) (Malvern Zetasizer, Nano-ZS). For TEM sample preparation, the nanogel solution (1.0 mg/ml) was dropped onto a carbon coated copper grid and dried using filter paper. The image was taken without any further processing. DLS measurement was done using 1.0 mg/ml nanogel solution in PBS.

Drug Release Study.

In vitro drug release from RPDSEG/DOX nanogel was performed in buffers (PBS pH 7.4, acetate buffer pH 5.5) with and without DTT at 37° C. using Spectra/Por® dialysis tube (MWCO, 1.0 kDa). The release medium containing 10 mM DTT was used for the sample to mimic the drug release under intracellular redox environment while acetate buffer of pH 5.5 was employed to mimic lysosomal condition. The nanogel solution (equivalent to 50 μg DOX) was transferred into dialysis tubing and immersed into pre-warmed buffer (40 mL). At predesigned time intervals, 1.0 mL of buffer outside the dialysis tube was sampled and the same amount of fresh buffer was replaced to make up the constant volume. The sample was freeze dried (24 h.), dissolved in DMSO: ddH2O (200 μL, 1:1 v/v) and DOX absorbance was measured through an UV-Vis spectrophotometer at λ=490 nm.

Figure 1B:
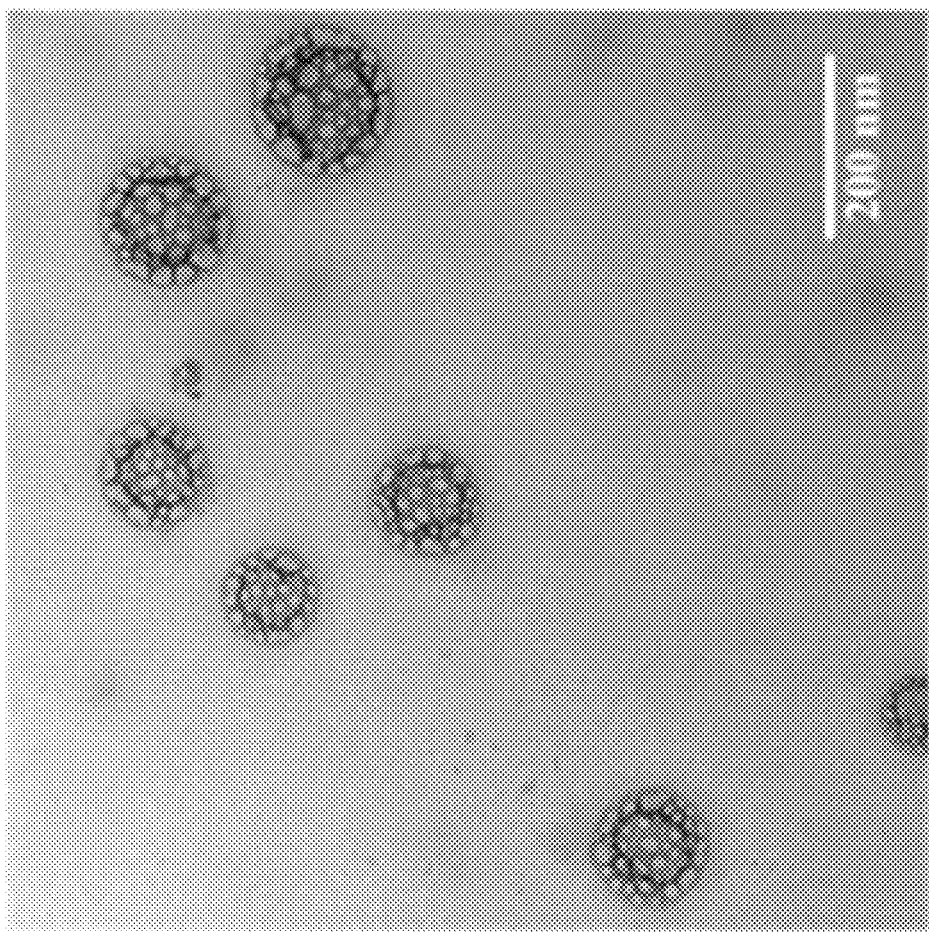
FIGS. 1B and 1C show, respectively, TEM images of a ND nanogel and a NCPD nanogel according to the Examples. Both images have a scale bar of 200 nm.
Figure 1C:
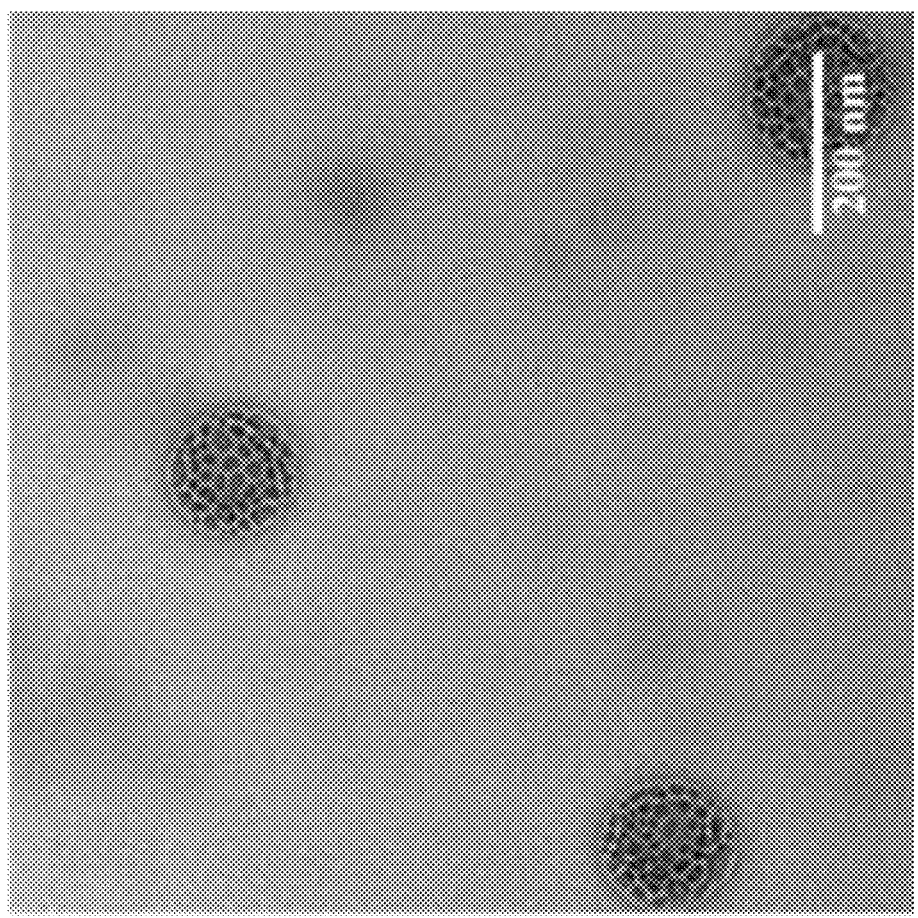

Results:

The polymer used for the nanoparticle fabrication was synthesized by free radical polymerization of 2(pyridin-2-yldisulfanyl)ethyl acrylate (PDSA) and poly(ethylene glycol) methacrylate (mPEG), and then modified with αVβ3 integrin targeting moiety, cyclo (Arg-Gly-Asp-D-Phe-Cys) (cRGD) peptide, by thiol-disulfide exchange reaction (FIG. 6A-6C). Drug loaded nanogels, ND (nano doxorubicin (DOX)) and NCPD (nano-cocktail of paclitaxel (PTX) and DOX), were fabricated by dialysis after the crosslinking reaction initiated by the addition of predetermined amount of tris(2-carboxyethyl)phosphine (TCEP). The formed intramolecular disulfide bonds triggered the assembly of the subcompartment of the nanogel while the disulfide bonds between subcompartments, mainly due to intermolecular disulfide bonds, stabilized the multicompartment nanogel structure. Dynamic light scattering showed that the sizes of ND and NCPD are about 115 and 134 nm, respectively, which are significantly smaller than the size of the PDSEG nanoparticle (FIG. 1). PDSEG nanoparticle displays negative surface charge due to the contribution of pyridine ring (FIG. S2). The ND and NCPD nanogels showed less negative zeta potential owing to the neutralization effect of encapsulated doxorubicin, which also resulted in the smaller size of ND and NCPD. Since the $IC_{50}$ of PTX for cancer cells is much lower than that of DOX, we achieved the NCPD loaded with PTX and DOX at the molar ratio of 1:47.2. Transmission electron microscopy (TEM) further confirmed that both ND and NCPD nanogel are spherical and have a narrow size distribution. As expected, TEM images also show that the nanoparticles were arranged in a distinct multicomponent pattern, which confirmed our hypothesis.

Figure 2A:
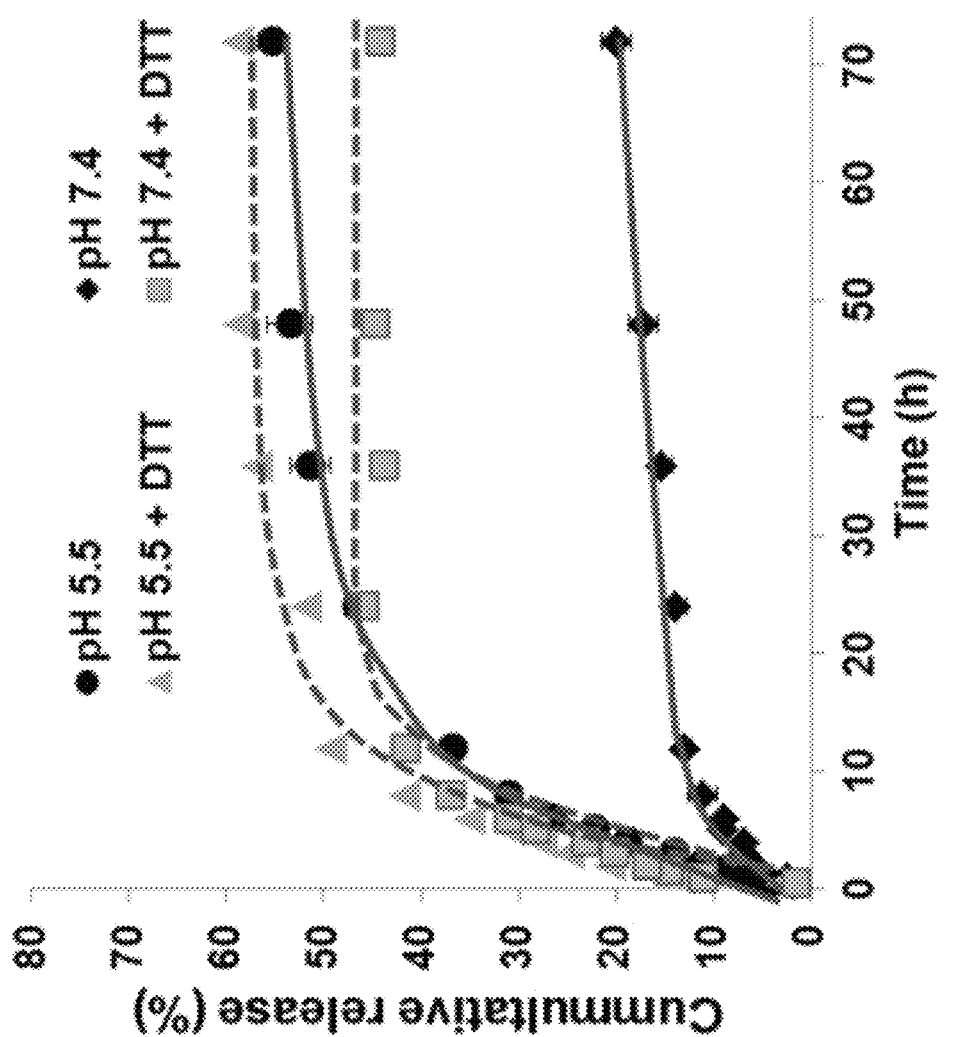
FIGS. 2A-2C show the ND nanogel drug releasing kinetics and its intracellular self-expanding, with FIG. 2A showing the drug release kinetics under different media conditions.
Figure 2B:
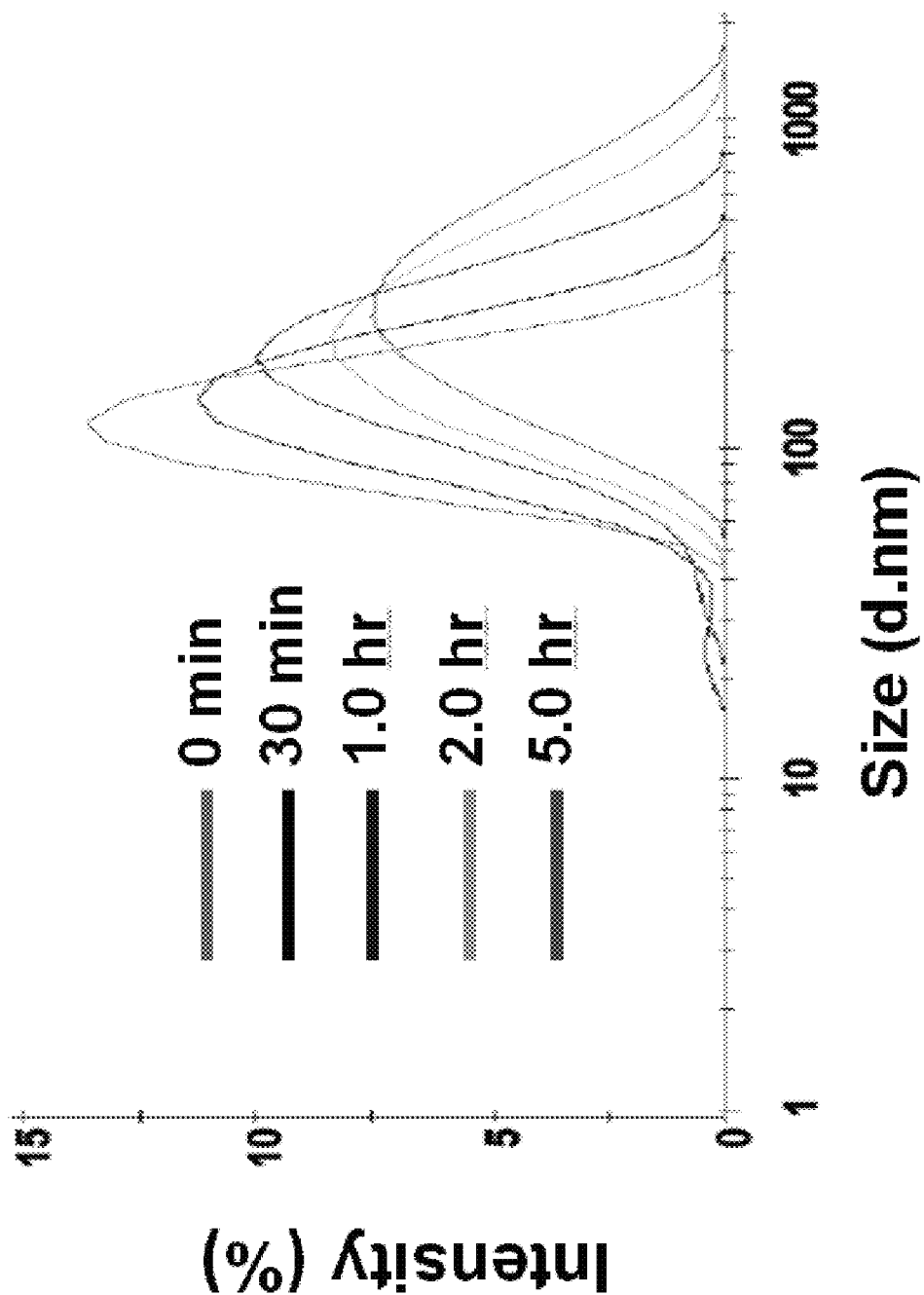
Figure 2C:
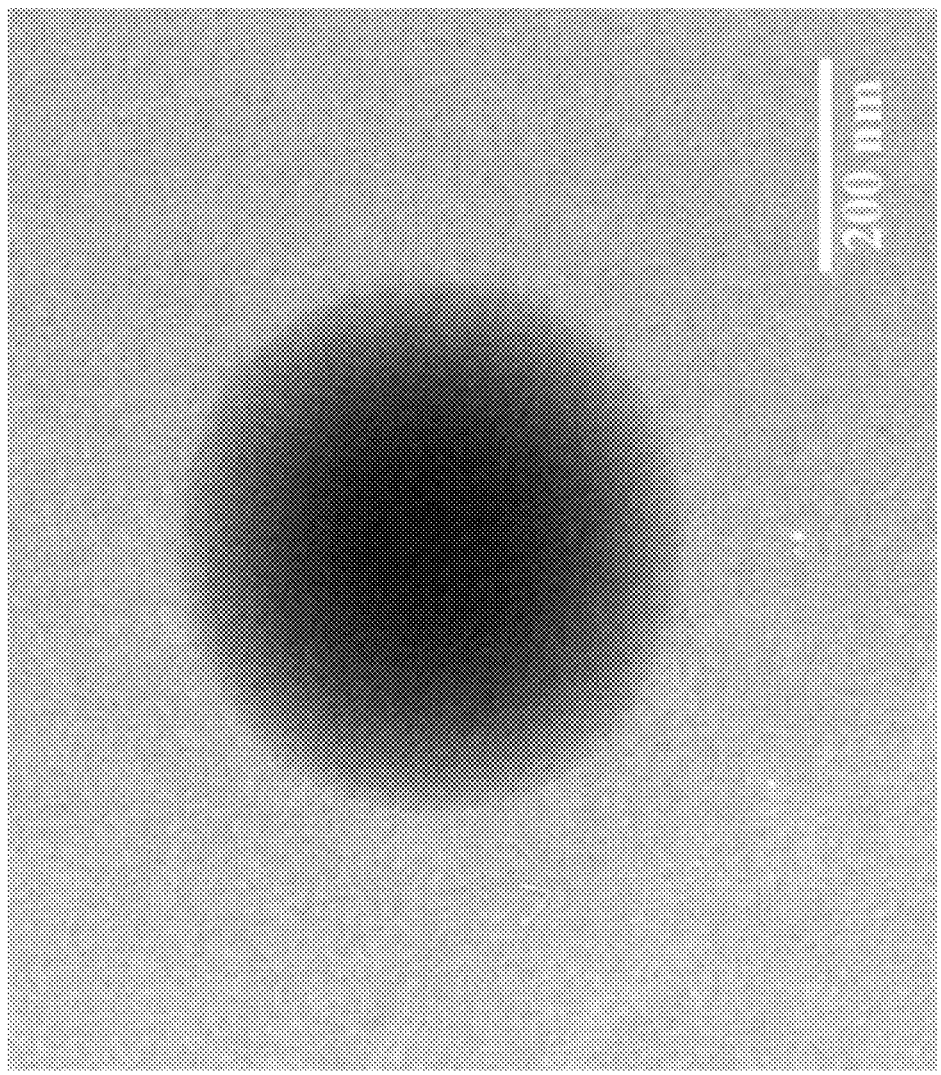

Since both ND and NCPD were made of the same polymer and fabricated from the same assembly method (except the loaded drugs), for simplification we used ND nanogel as a model to investigate the NCPD nanogel response to the stimuli of both pH and redox potential and its cellular uptake and intracellular trafficking. To validate the pH responsive property of the nanogel, we carried out the drug release kinetic measurement at both pH 7.4 and 5.5 to mimic the physiological and lysosomal pH. FIG. 2A showed that the release of doxorubicin from ND nanogel is heavily dependent on the pH of the environment. DOX release over 72 h in PBS (pH 7.4) was significantly lower (19.9±1.45%) than that in acetate buffer (pH 5.5) (55.2±1.53%). Similarly, we also found the release of DOX from ND is relies on the redox. Contrasting to the plane PBS, PBS supplemented with DTT (10 mM) induced significantly higher amount of DOX release, 44.21±1.2% over 72 h. The higher release in DTT containing medium was attributed to the reductive degradation of nanogel. However, there was no significant increase of drug released in the acetic buffer containing 10 mM DTT, which we think is due to both acidic pH and redox potential resulted in same side chain cleavage regardless the breaking points. To further investigate the intracellular behavior of the redox sensitive nanogel, we added TCEP to simulate the intracellular elevated glutathione condition. FIG. 2B showed that ND nanogel quickly increased its size from 113 nm to 262 nm after 5 hr incubation in PBS (pH 7.4 containing 1 mM of TCEP). Transmission electron microscopy also proved the enlargement of the nanogel (FIG. 2C). Since the ND nanoparticle is negatively charged, the cleavage of disulfide bonds will result in the swelling of the nanogel due to the repulsion force between charged polymer blocks. We expect the redox responsive swelling of the nanogel will break up the lysosome membrane and facilitate its trafficking to nuclei. It is worthy to note that the original clear multicompartment signature of the nanogel disappeared with the size increase. We think the loss of multicompartment pattern was due to the break of disulfide bonds and the reorganization of nanogel afterwards. Furthermore, both the loss of multicompartment signature and enlarged size suggest the formation of looser nanogel, which could contribute to faster drug release as shown in FIG. 2A.

Figure 3A:
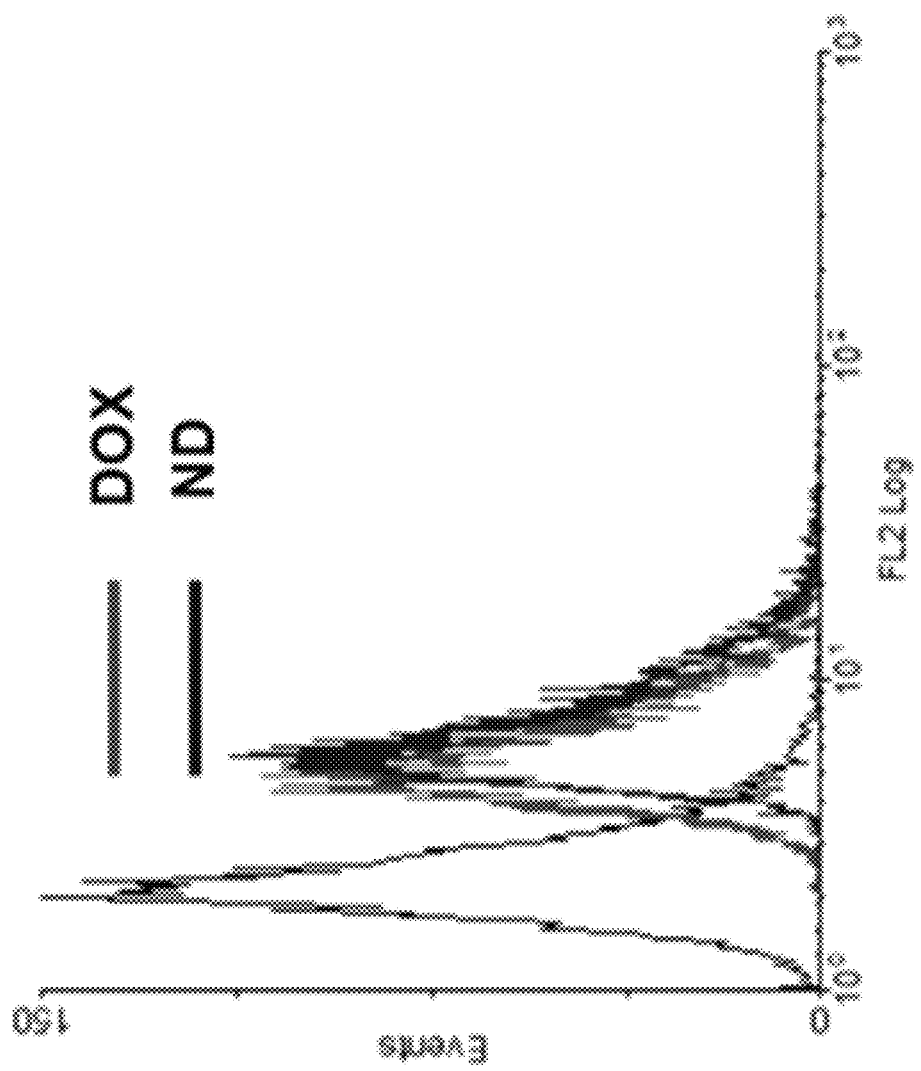
FIGS. 3A-3B show the cellular uptake of nanogel. HCT-116 cells treated with DOX and nanogel (equivalent to 0.5 μM DOX) for 3 h. Histogram (A) and percentage (B) of DOX positive population of cells derived from flow cytometry. Data represent the mean (±SD) of three individual experiments.
Figure 3B:
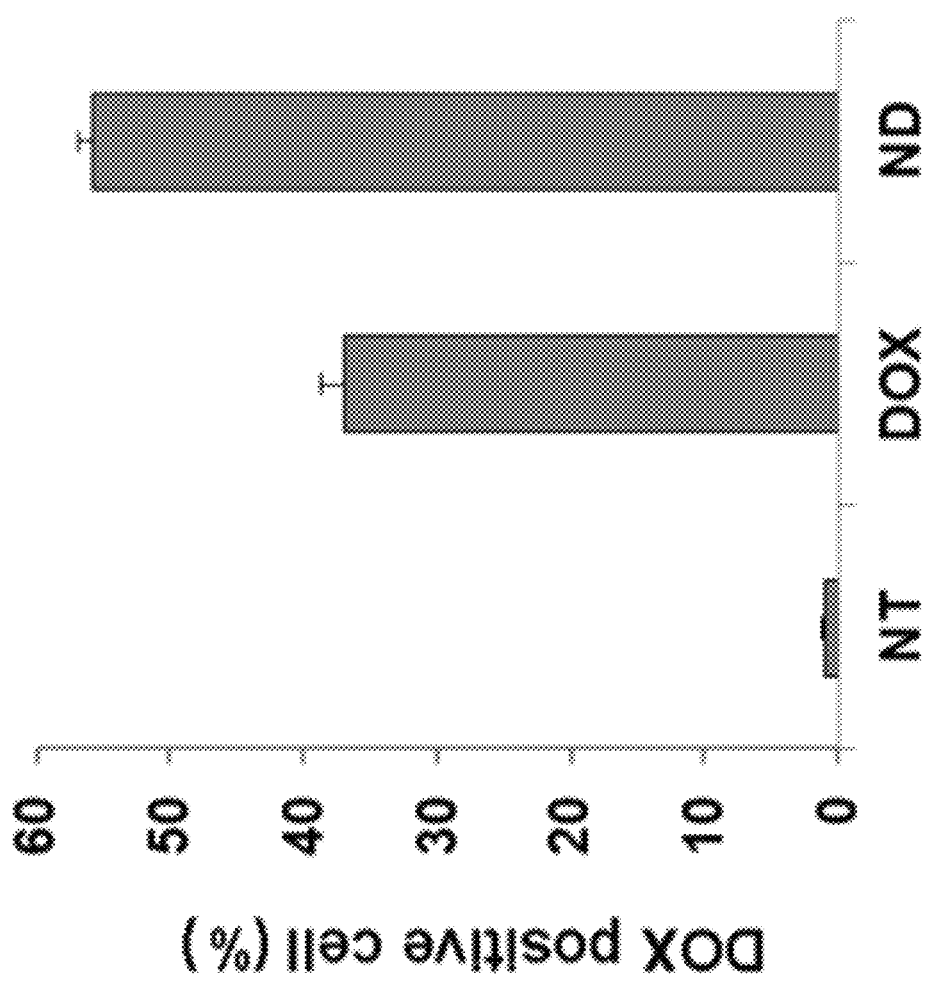

To enhance the nanogel targeting to cancer cells, cRGD peptides were conjugated with the PDSEG polymer by thiol-disulfide exchange reaction. The successful conjugation of RGD peptide was evidenced by the appearance of the peak at 375 nm by UV-Vis spectrophotometry. To our surprise, we found the conjugation of RGD peptide significantly increased the drug loading efficiency, from 12.06% to 40.42%. The cellular uptake of DOX loaded nanoparticle was quantified with flow cytometry. Nanogel without RGD modification was not included as control due to it far lower drug loading efficiency. Fluorescence-activated cell sorting (FACS) data indicate that Nanogel ND could enter HCT-116 colon cancer cells more efficiently than free DOX (FIG. 3).

To monitor the intracellular trafficking of nanogel, confocal laser scanning microscopy (CLSM) was employed. Free DOX enters cancer cells and preferentially labels their nuclei in 3 hr. Since only about 20% DOX could be released from nanogel under the intracellular environment (FIG. 2A), the signals should mainly represent ND nanogel. ND nanogel appeared mostly in the region close to nuclei in the same time period. Due to its relatively large size, it will be impossible for it to pass the nuclear pore complex, which is about 40 nm. The successful release of drugs was evidenced by the overlap of red (doxorubicin) and blue (nuclei dye, Hoechst 33342) signals after 12 hr treatment.

Figure 4A:
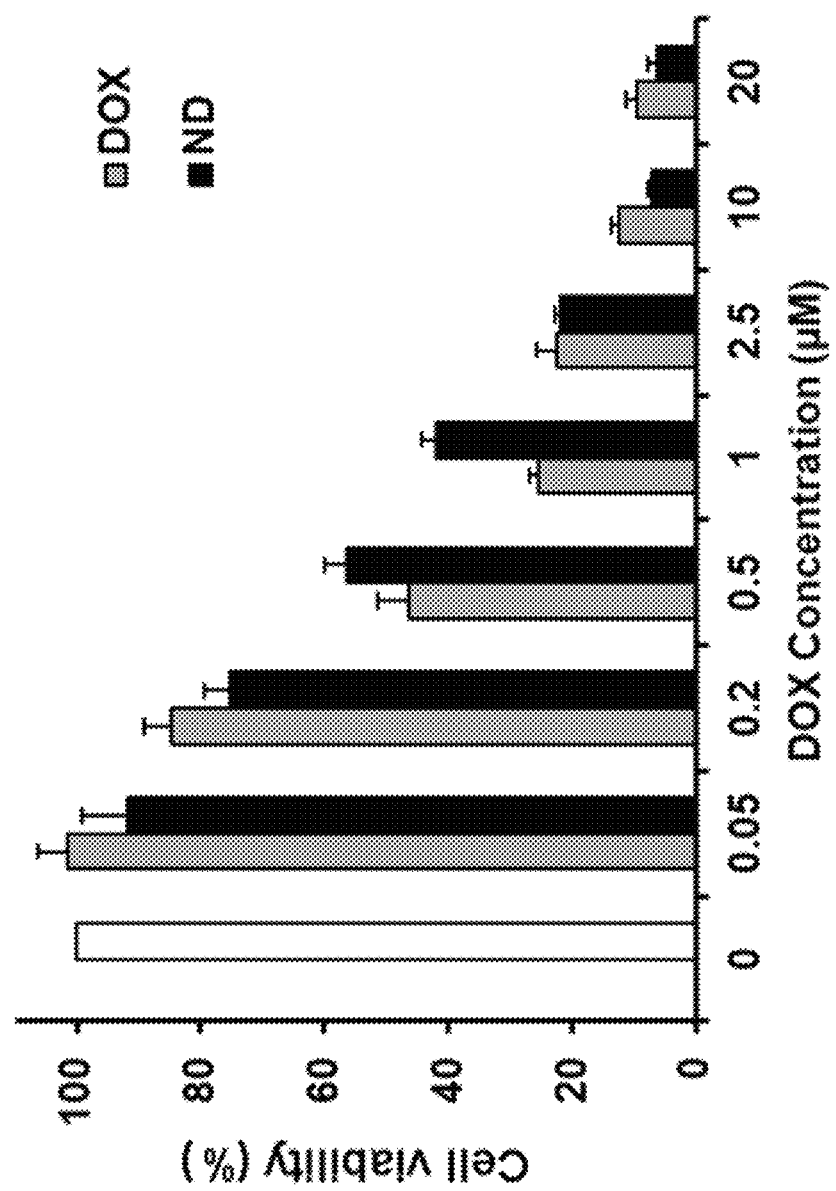
FIG. 4A-4B show the cytotoxicity of nano-cocktail for HCT-116 colon cancer cells, with 4A: Cells were treated with free DOX or ND nanogel for 72 hr and 4B: Cells were treated with the free drug alone, free drug cocktail (FPD) or NCPD with the combination of PTX and DOX in the molar ratio of 1:47.2 for 72 hr. The adopted free DOX concentrations were calculated based on its corresponding drug cocktail. Data represent the means (±SD) of three individual experiments. ($P<0.05$*; $P<0.01$ #).
Figure 4B:
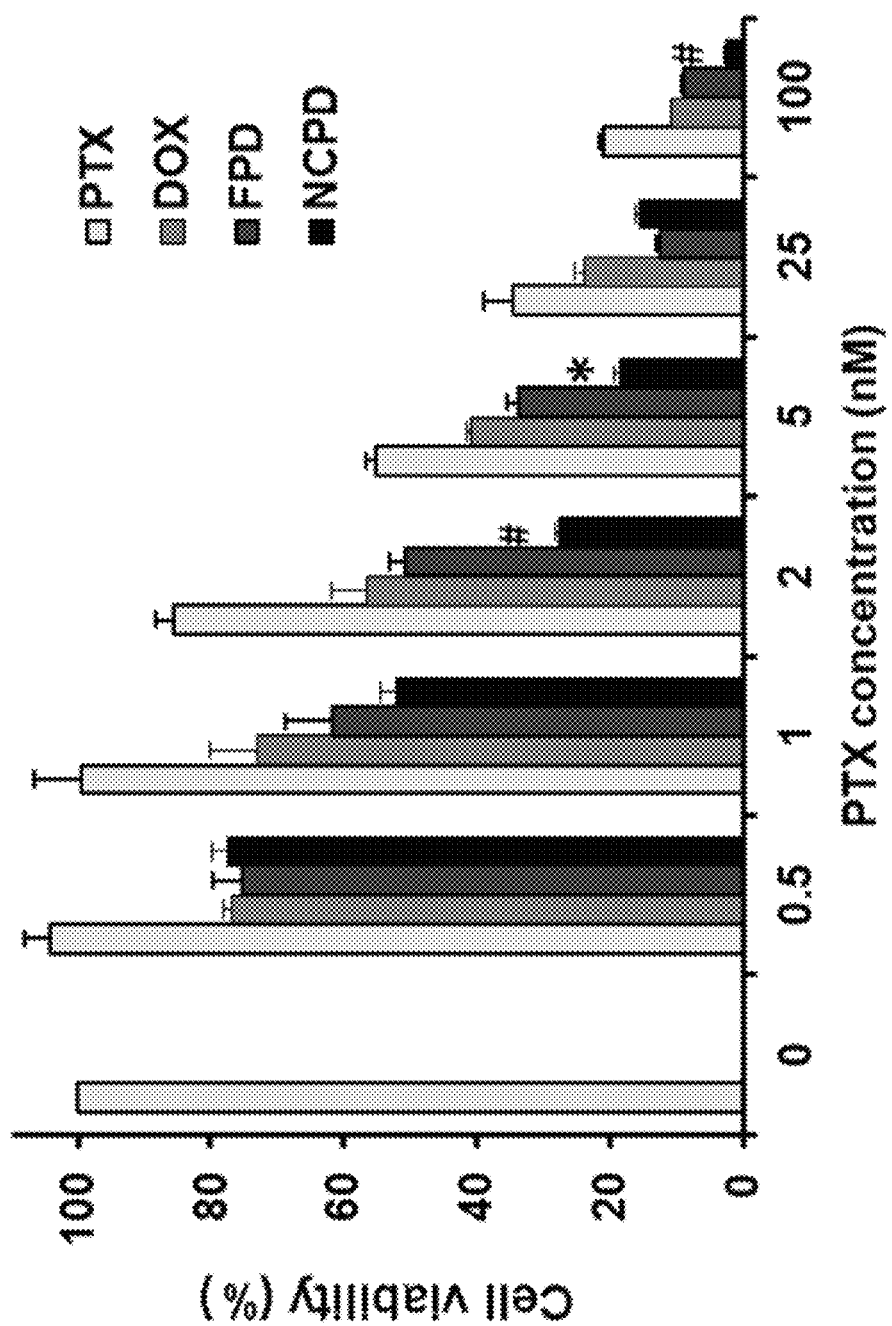

Finally, we examined the anticancer efficacy of the NCPD nanogel by (3-(4,5-Dimethylthiazol-2-yl)-2,5-diphenyltetra-zolium bromide (MTT) assay. PDSEG polymer itself didn't show any toxicity to HCT-116 colon cancer cells. The DOX loaded nanogel exhibited comparable anticancer efficacy to that of free DOX (FIG. 4A). The combination treatment of free PTX and DOX killed more cancer cells than any drug alone, which is consistent as literature reported. 12 NCPD showed significant higher anticancer efficacy than that of free drug cocktail (FIG. 4B). Furthermore, NCPD could kill almost all HCT-116 cancer cells at the PTX concentration of 100 nM while its free drug counterpart no longer showed a dose-responsive effect.

Figure 5:
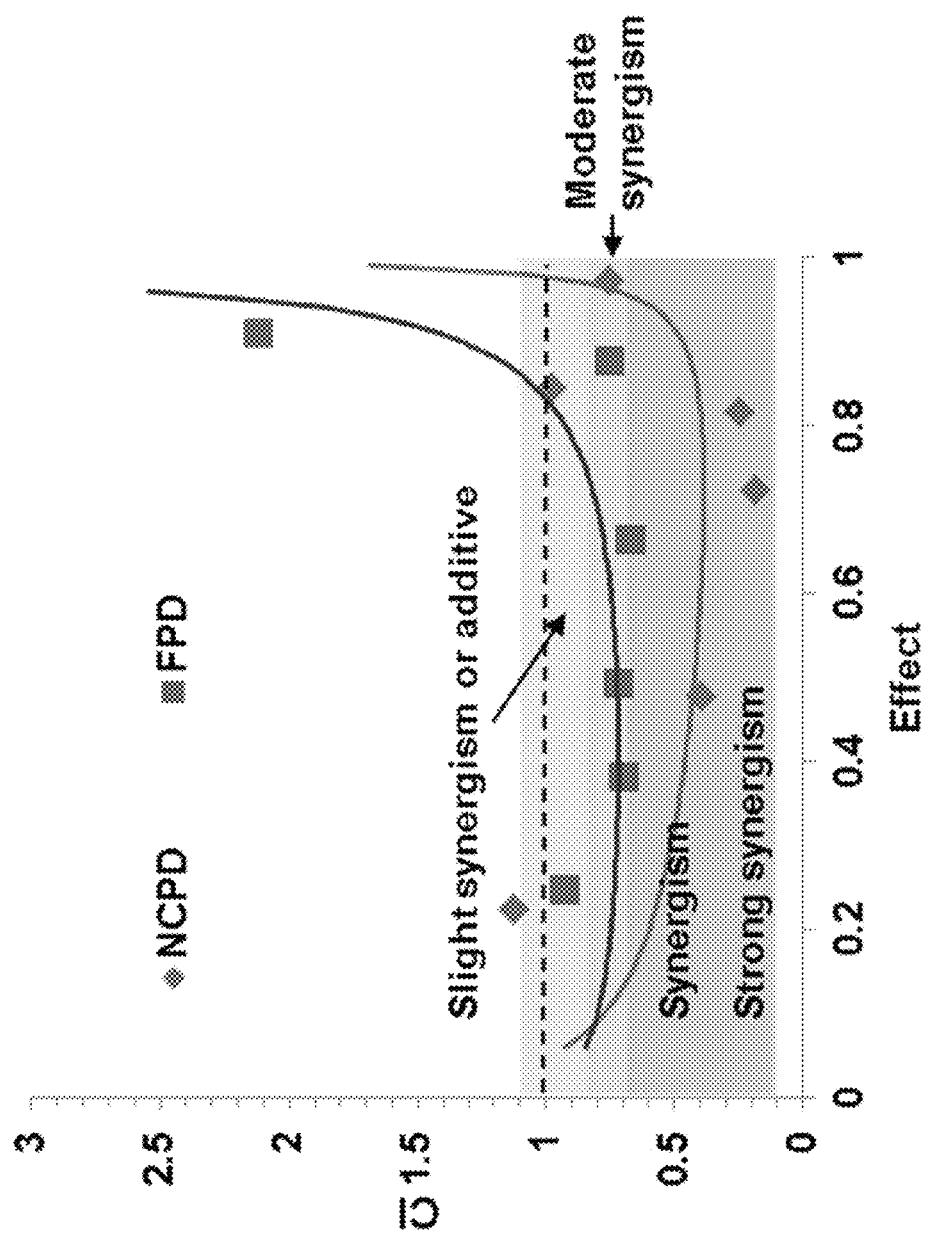
FIG. 5 shows the combination index values (CI) vs drug effect for free drug combination (FPD) and nano-cocktail NCPD). Cells were treated with combination of PTX and DOX in the molar ratio of 1:47.2. The solid lines represent the simulated combination index values at all effect levels as calculated by the CalcuSyn software for FPD and NCPD treatment, respectively. General CI values and their corresponding drug combination effects are: CI 0.1-0.3, strong synergism; CI 0.3-0.7, synergism; CI 0.7-0.85, moderate synergism; CI 0.85-0.90, slight synergism; CI 0.90-1.10, nearly additive. Data are derived from three individual experiments.

To determine whether PTX and DOX combination affected each other in an antagonistic, additive or synergistic manner, combination index (CI) analysis based on Chou-Talalay method was performed using CalcuSyn software. Generally, the CI values lower than 1 are considered as synergistic effect. The smaller the CI value, the stronger the synergistic effect. FIG. 5 showed that free DOX and PTX combination exhibited slight to moderate synergism in the killing of HCT-116 colon cancer cells. Interestingly, CI analysis also revealed that NCPD nano-cocktail displays much stronger synergism than its free drug counterpart.

Figure 7:
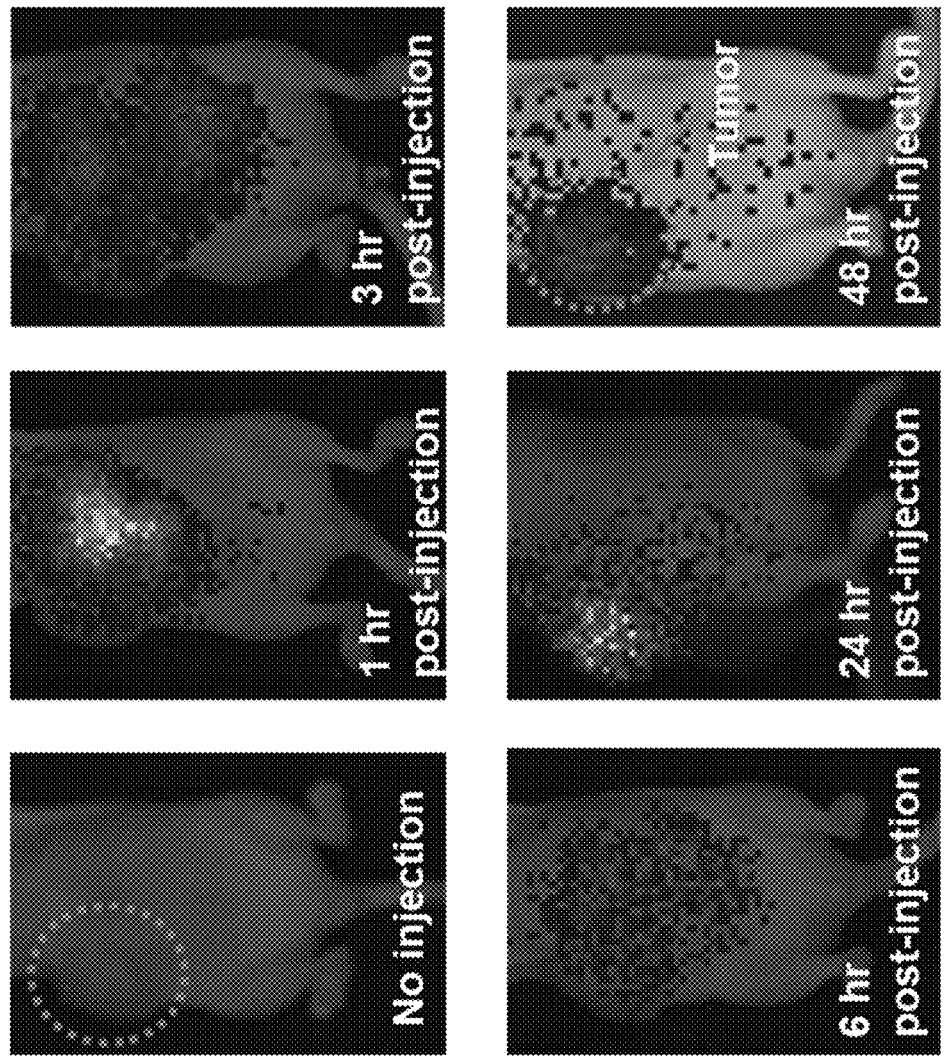
FIG. 7 shows the results of in vivo testing within mice according to the Examples.

In Vivo Results:

NCPD nanogel was labeled with a far-red fluorescence dye Cy7 and used to track the biodistribution of NCPD nanogel. A mouse xenograft tumor model created from SKOV-3 ovarian cancer cells was employed since SKOV-3 cells overexpress $\alpha_v\beta_3$ integrin which can be targeted by RGD peptide. For the fluorescence labeling of NCPD, PDSEG polymer was reacted with cysteamine to introduce carboxylic acid reactive group through thiol-disulfide exchange reaction and then reacted with Cy7-NHS with help of EDC and NHS. NCPD nanogel suspension was administered by retro-orbital injection. The distribution of nanogel was monitored with IVIS living animal imaging system. FIG. 7 showed that NCPD nanogel could selectively accumulate in the tumor tissue 24 and 48 hr post-injection These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a copolymer, the method comprising:
   polymerizing 2-(pyridin-2-yldisulfanyl)ethyl acrylate with poly(ethylene glycol)methacrylate via free radical polymerization to form the copolymer, wherein the copolymer comprises 2-(pyridin-2-yldisulfanyl)ethyl acrylate repeating units and poly(ethylene glycol)methacrylate repeating units, and wherein the molar ratio of 2-(pyridin-2-yldisulfanyl)ethyl acrylate to poly(ethylene glycol)methacrylate is about 100:1 to about 1:100.

2. The method of claim 1, wherein the free radical polymerization is initiated by 2,2-azobisisobutyronitrile.

3. The method of claim 1, wherein the poly(ethylene glycol)methacrylate has the structure of Formula (II):

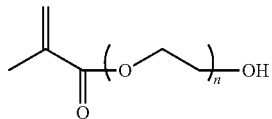

(II)

where n is about 6 to about 3,000.

4. The method of claim 1, wherein the copolymer is a random copolymer or block copolymer.

5. The method of claim 1, comprising:
   after polymerizing, reacting the copolymer with a thiol monomer that contains a carbon-bonded sulfhydryl through a thiol-disulfide exchange reaction to modify end groups on a first portion of the 2-(pyridin-2-yldisulfanyl)ethyl acrylate repeating units.

6. The method of claim 5, wherein about 1 molar % to about 50 molar % of the 2-(pyridin-2-yldisulfanyl)ethyl acrylate repeating units in the copolymer are converted with the thiol monomer that contains a carbon-bonded sulfhydryl through a thiol-disulfide exchange reaction.

7. The method of claim 5, wherein the thiol monomer has the structure of Formula (V):

(V)

where m is 1 to 19 and R1 is H, a hydroxyl group, a carboxyl group, an aldehyde group, an amine group, an amide group, an amino acid, a peptide chain of at least two amino acids, or another organic end group.

8. The method of claim 5, further comprising:
   thereafter, crosslinking the copolymer via a thiol-disulfide exchange reaction to form a crosslinked copolymer.

9. The method of claim 8, wherein crosslinking the copolymer is facilitated by a crosslinking agent.

10. The method of claim 9, wherein the crosslinking agent comprises tris(2-carboxyethyl)phosphine.

11. The method of claim 8, further comprising:
loading a drug into the crosslinked copolymer.

12. A copolymer comprising 2-(pyridin-2-yldisulfanyl)ethyl acrylate repeating units of Formula (III):

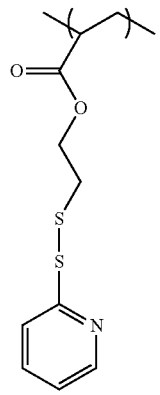

(III)

and poly(ethylene glycol)methacrylate repeating units of Formula (IV):

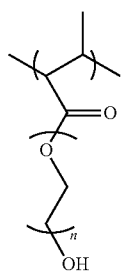

(IV)

wherein n is about 6 to about 3,000.

13. The copolymer of claim 12, wherein the 2-(pyridin-2-yldisulfanyl)ethyl acrylate repeating units of Formula (III) and the poly(ethylene glycol)methacrylate repeating units of Formula (IV) are present in the polymer in a molar ratio of about 100:1 to about 1:100.

14. The copolymer of claim 12, wherein the 2-(pyridin-2-yldisulfanyl)ethyl acrylate repeating units of Formula (III) and the poly(ethylene glycol)methacrylate repeating units of Formula (IV) are present in the polymer in a molar ratio of about 20:1 to about 1:20.

15. The copolymer of claim 12, wherein the copolymer has a molecular weight of about 1,000 to about 100,000.

16. The copolymer of claim 12, further comprising modified disulfanyl repeating units of Formula (VI):

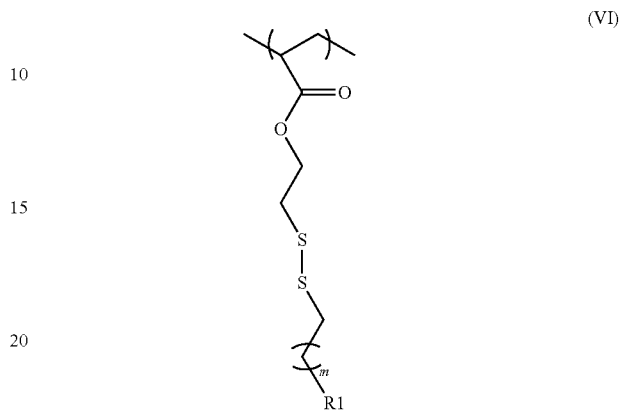

(VI)

where R1 is H, a hydroxyl group, a carboxyl group, an aldehyde group, an amine group, an amide group, an amino acid, a peptide chain of at least two amino acids, or another organic end group; and m is an integer of 1 to about 19.

17. The copolymer of claim 16, wherein the modified disulfanyl repeating units are present in the copolymer in an amount that is about 1 molar % of the 2-(pyridin-2-yldisulfanyl)ethyl acrylate repeating units in the modified copolymer to about 50% of the 2-(pyridin-2-yldisulfanyl)ethyl acrylate repeating units in the modified copolymer.

18. The copolymer of claim 16, wherein the copolymer is crosslinked upon a portion of the 2-(pyridin-2-yldisulfanyl)ethyl acrylate repeating units.

19. A nanogel comprising the copolymer of claim 18 and a drug loaded within the nanogel.

20. A method of targeted delivery of a drug to cancer cells, the method comprising:
administering the nanogel of claim 19 to a patient.

* * * * *